United States Patent [19]

Shoesmith, deceased

[11] Patent Number: Plant 5,972

[45] Date of Patent: May 5, 1987

[54] CHRYSANTHEMUM PLANT NAMED BINGO

[75] Inventor: Leonard H. Shoesmith, deceased, late of Westfield, England, by May V. Shoesmith, executrix

[73] Assignee: Ball Pan Am Plant Company, Parrish, Fla.

[21] Appl. No.: 712,695

[22] Filed: Mar. 18, 1985

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Chrysanthemum named Bingo having a dwarf habit, round capitulum form and button capitulum type, yellow ray florets, none to few disc florets, eight week response, excellent keeping quality, and an ability to be grown year around in 9 cm. pots with little growth regulation.

1 Drawing Figure

The present invention comprises a new and distinct cultivar of *Chrysanthemum morifolium,* Ramat., hereinafter referred to by the cultivar name Bingo.

Bingo is a product of a planned breeding program which had the objective of creating new Chrysanthemum cultivars with eight (8) week response, yellow button type flowers, and dwarf habit for year around growing in 9 cm. pots. Such traits in combination were not present in previously available commercial cultivars.

Bingo was originated from a hybridization made by Leonard H. Shoesmith in a controlled breeding program in Westfield, Woking, England in 1978. The male and female parents are unknown at this time. Bingo was discovered and selected as one flowering plant within the progeny of the parentage by applicant in November, 1979 in a controlled environment in West Chicago, Ill., and given the code name FG9-1816-BS.

The first act of asexual reproduction of Bingo was accomplished when vegetative cuttings were taken from the initial selection in February, 1980 in a controlled environment in West Chicago, Ill. by a technician working under formulations established and supervised by Leonard H. Shoesmith. Horticultural examination of selected units initiated in March, 1980 has demonstrated that the combination of characteristics as herein disclosed for Bingo are firmly fixed and are retained through successive generations of asexual reproduction.

Bingo has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Bingo, which in combination distinguish this Chrysanthemum as a new and distinct cultivar:

1. Round capitulum form.
2. Button capitulum type.
3. None to few disc florets.
4. Yellow ray florets.
5. Eight (8) week response.

6. Dwarf habit, 10–15 cm. above edge of pot when properly grown.
7. Ability to be grown year around in 9 cm. pots requiring little B-9 treatment.
8. Exceptional keeping quality (up to six (6) weeks) in an air conditioned room (70°–80° F.).

Of the many commercial cultivars known to the present inventor, the most similar in comparison to Bingo is the cultivar Butterball, disclosed in U.S. Plant Pat. No. 4,556. In comparison to Butterball, Bingo has a more dwarf habit, is one week earlier in response, and requires less B-9. The flower form and color of Bingo are similar to those same characteristics of Butterball.

The accompanying photographic drawing shows typical inflorescense characteristics of Bingo, with colors being as nearly true as possible with illustrations of this type. The photograph is in black and white, with a single flower being colored to accurately depict true flower color.

In the following description color references are made to The Royal Horticultural Society Colour Chart. The color values were determined at approximately 11:00 a.m. on Jan. 17, 1985 under natural and fluorescent light at Bradenton, Fla.

Classification:

*Botanical.*—*Chrysanthemum morifolium,* Ramat., CV Bingo.

*Commercial.*—Button spray, four (4) inch pot.

I. INFLORESCENCE

A. Capitulum:

*Form.*—Flat.

*Type.*—Button.

*Diameter across face.*—2.5 cm.–4 cm.

B. Corolla of ray florets:

*Color (general tonality from a distance of three meters).*—Yellow.

*Color (under surface).*—9 B.

*Color (top surface).*—9 A.

C. Corolla of disc florets:

*Color (mature).*—Yellow.

*Color (immature).*—Lime Yellow.

D. Reproductive organs:

*Androecium.*—Present in disc florets only; few in number.

*Gynoecium.*—Present in both ray and disc florets; numerous.

II. PLANT

A. General appearance:

*Height.*—10–15 cm. above edge of pot when properly grown.

B. Foliage:

*Color* (*under surface*).—148 B.

*Color* (*top surface*).—137 A.

*Shape.*—Ovate and deeply lobed.

It is claimed:

1. A new and distinct cultivar of Chrysanthemum named Bingo, as described and illustrated, and particularly characterized by its dwarf habit; round capitulum form and button capitulum type; yellow ray florets; none to few disc florets; eight week response; excellent keeping quality, and by its ability to be grown year around in 9 cm. pots with little growth regulation.

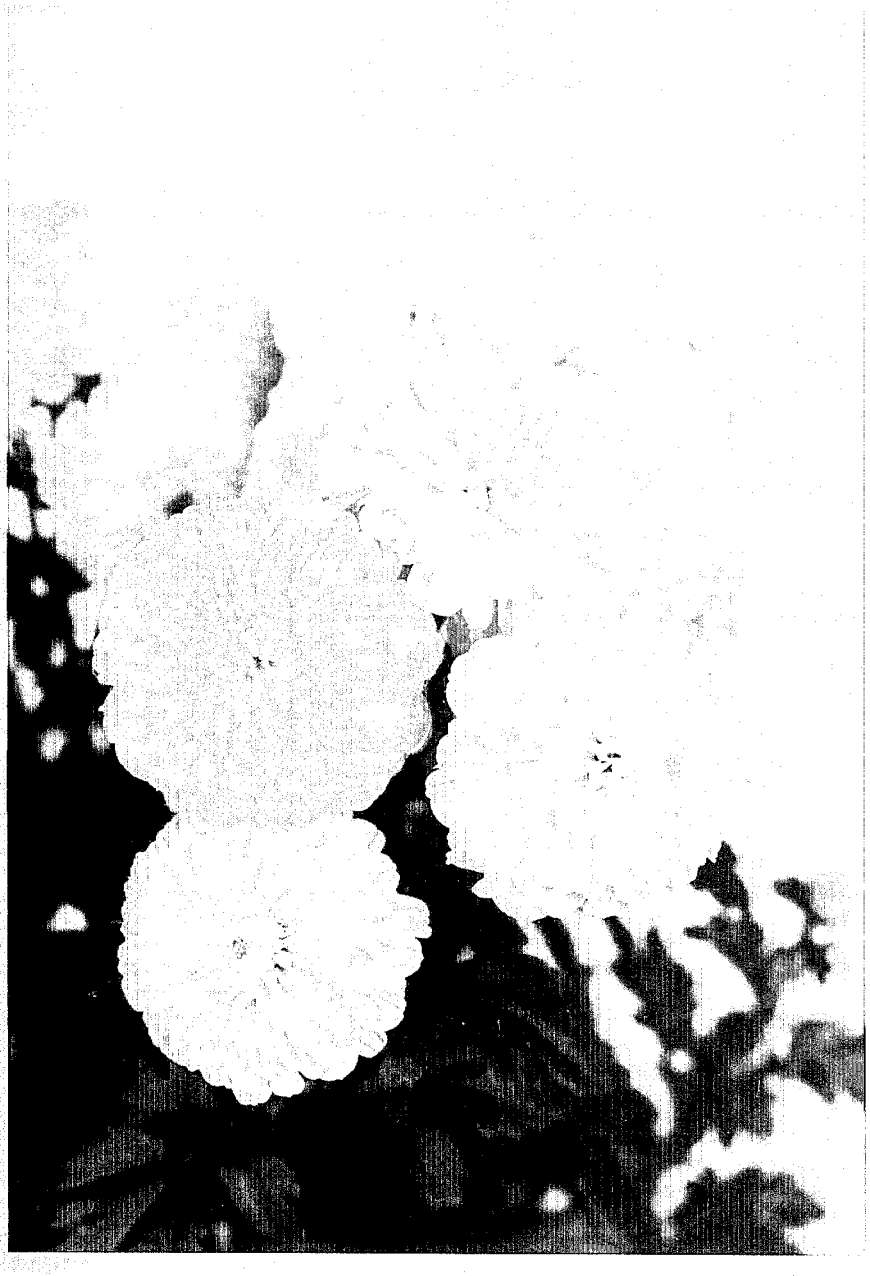

* * * * *